(12) United States Patent
Carron et al.

(10) Patent No.: US 9,459,146 B2
(45) Date of Patent: *Oct. 4, 2016

(54) SPECTROMETER

(71) Applicant: MKS TECHNOLOGY, Centennial, WY (US)

(72) Inventors: Keith Carron, Centennial, WY (US); Mark Watson, Laramie, WY (US); Shane Buller, Laramie, WY (US)

(73) Assignee: MKS Technology, Centennial, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/518,855

(22) Filed: Oct. 20, 2014

(65) Prior Publication Data

US 2015/0099292 A1    Apr. 9, 2015

Related U.S. Application Data

(63) Continuation of application No. 13/161,485, filed on Jun. 15, 2011, now Pat. No. 8,867,033.

(60) Provisional application No. 61/355,136, filed on Jun. 15, 2010.

(51) Int. Cl.
*G01J 3/02* (2006.01)
*G01J 3/44* (2006.01)
*G01N 21/65* (2006.01)

(52) U.S. Cl.
CPC ............ *G01J 3/0237* (2013.01); *G01J 3/0208* (2013.01); *G01J 3/44* (2013.01); *G01J 3/4412* (2013.01); *G01N 21/65* (2013.01)

(58) Field of Classification Search
USPC ........................................................ 356/326
See application file for complete search history.

(56) References Cited

U.S. PATENT DOCUMENTS

2008/0194044 A1*  8/2008  Faris et al. .................... 436/537

* cited by examiner

*Primary Examiner* — Tarifur Chowdhury
*Assistant Examiner* — Omar Nixon
(74) *Attorney, Agent, or Firm* — Dinsmore & Shohl LLP

(57) ABSTRACT

A spectroscopic system is provided. In one embodiment, the spectroscopic system comprises a light source adapted to provide a beam of illumination; an optical system adapted to provide the beam of illumination to a sample and receive a spectroscopy signal from the sample and direct the spectroscopy signal to at least one single channel detector, wherein the optical system comprises an adjustable dispersing element for directing one or more spectral features of the spectroscopy signal to the at least one single channel detector; a calibration detector adapted to determine a set point of the adjustable dispersing element; and a source synchronization component adapted to synchronize an operation of the light source and the at least one single channel detector. A method of calibrating a dispersing element of a spectrometer is also provided.

18 Claims, 9 Drawing Sheets

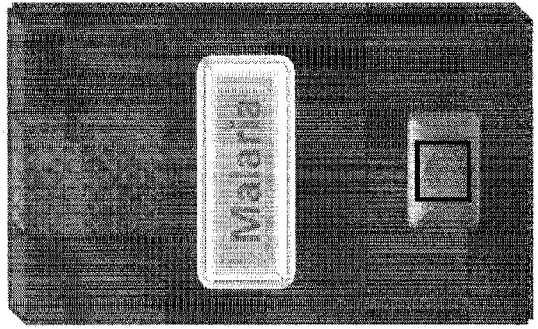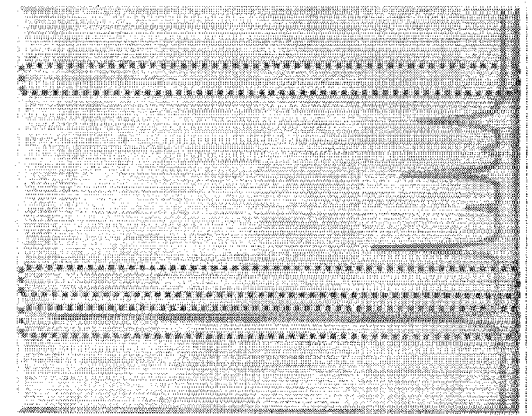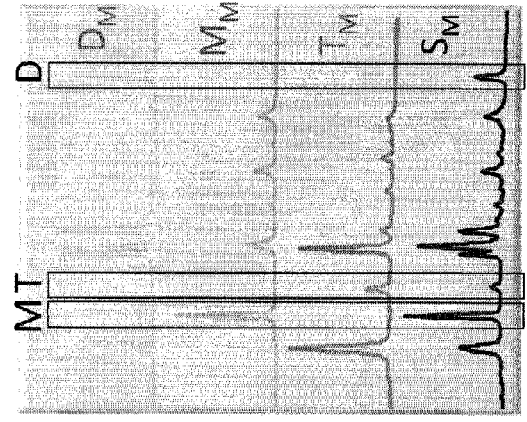
FIGURE 6

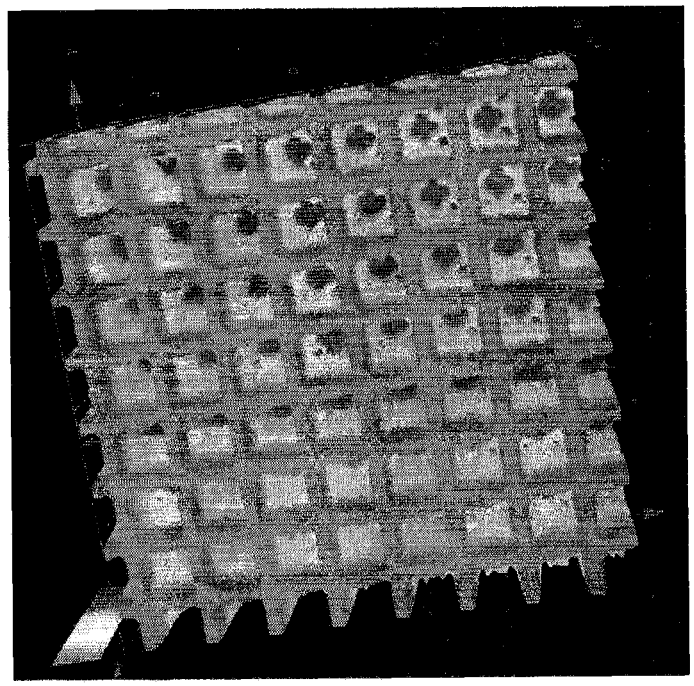
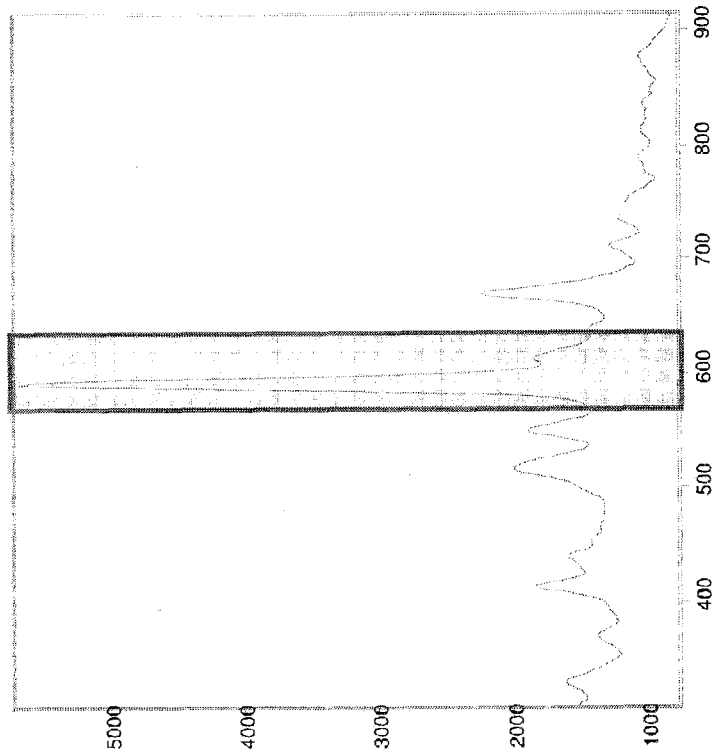
FIGURE 7

SPECTROMETER

CROSS-REFERENCE TO RELATED APPLICATIONS

This application is a continuation of U.S. application Ser. No. 13/161,485 entitled "Spectrometer" filed on Jun. 15, 2011, which is hereby incorporated by reference in its entirety as though fully set forth herein. This application also claims the benefit of U.S. provisional application No. 61/355,136 entitled "Raman Spectrometer" and filed 15 Jun. 2010, which is also hereby incorporated by reference as though fully set forth herein.

BACKGROUND

Spectroscopy is a general term for the process of measuring energy or intensity as a function of wavelength in a beam of light or radiation. Spectroscopy uses absorption, emission, or scattering of electromagnetic radiation by atoms, molecules or ions to qualitatively and quantitatively study physical properties and processes of matter.

A typical Raman spectrometer, for example, identifies a sample of an unknown material by measuring intensities across a spectrum of light or radiation received from the sample. A sampled spectrum is then matched against a library of known Raman spectra to identify the sample of unknown material. The sampled spectrum is matched to a known spectrum within the library using algorithms that map the correlation between the unknown spectrum and the library spectra. One example of a Raman spectrometer is disclosed in U.S. Pat. No. 7,403,281 entitled "Raman Spectrometer" and issued to Keith T. Canon et al. on Jul. 22, 2008, which is incorporated herein by reference as if fully set forth herein.

A spectrometer, for example, can disperse the light or radiation and use an array detector, such as a charge coupled device detector, to collect an array of data points that can be used to reconstruct the spectra. A laser excitation source is highly stabilized in the frequency domain so that a sampled spectrum can be precisely measured against the library of known Raman spectra.

Raman reporters or tags having known spectra can be used in a spectroscopic system. In one particular application, for example, nanoparticles tagged with specific coatings constitute Raman reporters or tags that have a very large Raman signal due to the phenomenon known as Surface Enhanced Raman Scattering (SERS). Raman reporters or tags are typically used in medical assays, brand security, and military applications. These applications differ from Raman material identification in that the sample Raman spectrum is not used to identify an unknown material. Rather, the Raman spectrum of a tag is known. In some applications, multiple tags (e.g., up to 50 tags) are used having different Raman spectra.

SUMMARY

In one embodiment, a "Raman reader" rapidly scans for anticipated Raman feature regions. By looking at one or more specific frequencies, instead of a whole spectrum, such a reader can identify one or more specific feature(s) precisely with a large signal to noise ratio. The reader can also maintain an accurate frequency calibration to account for laser shifts or mechanical loss of frequency calibration.

In one embodiment, the spectroscopic system comprises a light source adapted to provide a beam of illumination; an optical system adapted to provide the beam of illumination to a sample and receive a spectroscopy signal from the sample and direct the spectroscopy signal to at least one single channel detector, wherein the optical system comprises an adjustable dispersing element for directing one or more spectral features of the spectroscopy signal to the at least one single channel detector; a calibration detector adapted to determine a set point of the adjustable dispersing element; and a source synchronization component adapted to synchronize an operation of the light source and the at least one single channel detector.

In one embodiment, the method comprises determining a set point along a path of an adjustable dispersing element, wherein the set point corresponds to a position of the dispersing element where a calibration signal of a spectrometer is detected at a calibration sensor of the spectrometer; adjusting the position of the dispersing element along the path by a predetermined offset measurement from the set point; and directing at least a portion of a spectroscopic signal from the dispersing element to a spectroscopic signal detector of the spectrometer.

BRIEF DESCRIPTION OF THE DRAWINGS

FIG. 6 shows an example method of performing an assay.

FIGS. 7 and 8 show an example method and system for three-dimensional imaging of Raman features of a sample.

Figure 1:
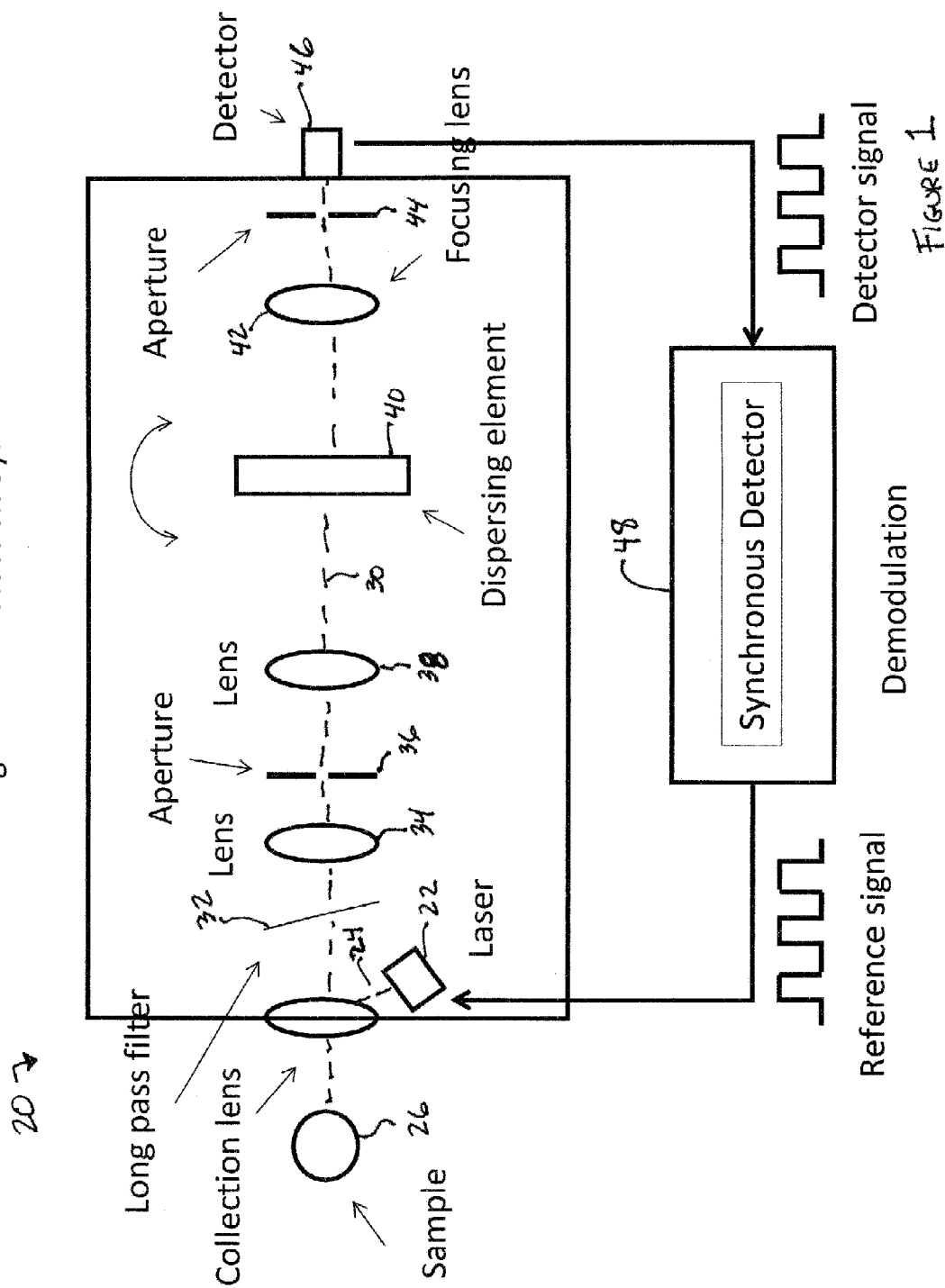
FIG. 1 shows one example embodiment of a Raman spectrometer.

While the technology is amenable to various modifications and alternative forms, specific embodiments have been shown by way of example in the drawings and are described in detail below. The intention, however, is not to limit the invention to the particular embodiments described.

DETAILED DESCRIPTION

In one embodiment, a "Raman reader" rapidly scans for anticipated Raman feature regions. By looking at one or more specific frequencies, instead of a whole spectrum, such a reader can identify one or more specific feature(s) precisely with a large signal to noise ratio. The reader can also maintain an accurate frequency calibration to account for laser shifts or mechanical loss of frequency calibration.

In a spectroscopy system with a relatively limited number of tags or target analytes, for example, a spectrometer need not look at an entire Raman spectrum, but may look for a limited number of spectral features that are known to occur with the tags or analytes of interest. Thus, the spectrometer does not need to waste time looking at regions of a Raman spectrum where the tags or analytes do not have unique spectral features. Rather, the tags may be identified with one or more limited spectral feature(s) even where very few tags or analytes are present. Therefore, a Raman spectrometer that has a high sensitivity to one or more specific spectral features, rather than to a full Raman spectrum, may be used to quickly identify tags or target analytes.

While a traditional Raman spectrometer might have an array detector (e.g., charge coupled device (CCD) array) that can read a whole spectrum at once where a Raman spectrum can take any shape or form, a Raman assay reader might only need to detect one or more anticipated spectra that are known in advance. While an array detector, such as a CCD array, could be used, higher signal to noise detection techniques can be used. A method of phase sensitivity detection with a modulated laser can produce improvements in signal to noise ratios versus a CCD array detector (e.g., thousand fold improvements).

Although traditional Raman systems have been reported using a phase sensitive detector such as a lock-in amplifier, the systems are designed to scan a spectrum by adjusting a position of a dispersing element (e.g., by rotating a grating). The rotation of the grating, for example, can introduce mechanical instabilities that cause the system to not have calibrated frequencies. Although calibration has been made with a neon emission spectrum or a standard Raman sample and spectrum, such an approach is not practical for a rapid Raman assay.

Figure 2:
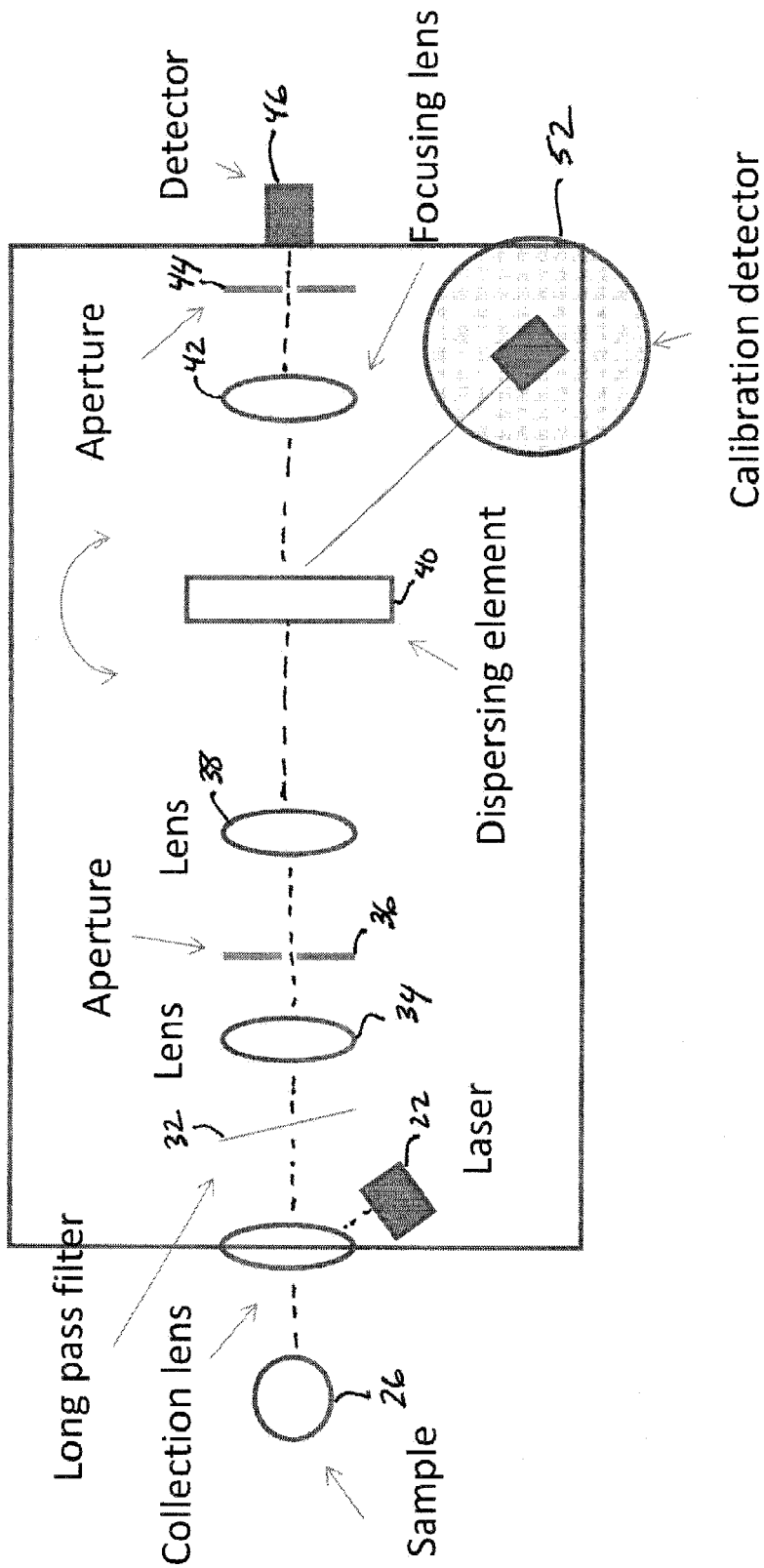
FIG. 2 shows another example embodiment of a Raman spectrometer that includes a calibration detector.

In one embodiment discussed herein, a photodiode or other detector is used to determine a position of a dispersing element of a spectrometer before or as the anticipated Raman features are examined (see, e.g., FIG. 2). The use of such a detector, for example, allows a Raman reader to compensate for mechanical variations in the spectrometer (e.g., of a movable grating or other dispersing element) and/or variations in a frequency of an excitation source.

In one particular embodiment, a reader also includes a mechanism to agitate a sample to provide mixing of reagents and a mechanism for separating positive tag pairs from negative tags, however, these functions may be performed independently of the reader as well. In one embodiment, for example, a positive nanoparticles tag can be paired with a paramagnetic particle where the particles are coupled with an analyte. Alternatively, a positive might be determined when a Raman reporter paramagnetic particle combination produces an anticipated Raman signal when a sample contains the analyte.

FIG. 1 shows one example embodiment of a Raman spectrometer 20. As shown in FIG. 1, the Raman spectrometer comprises an excitation source 22. The excitation source 22 typically comprises a laser light source. In one embodiment, for example, the excitation source 22 comprises a diode laser. A diode laser, for example, is capable of providing a plurality of wavelengths from the excitation source 22. The spectrometer 20 may further comprise a filter that filters the output of the excitation source 22, such as removing spurious emissions from the excitation source 22.

The spectrometer 20 further comprises a means for directing an incident beam 24 toward a sample 26. The means for directing the incident beam toward the sample comprises an optical system of the spectrometer 20 that directs the incident beam 24 toward the sample 26. In the embodiment shown in FIG. 1, for example, the optical system comprises a collection lens 28 that receives the incident beam 24 from the excitation source 22 and directs it to the sample 26. The collection lens 28, for example, may comprise a focusing lens in the path of the incident beam 24 that couples the incident beam 24 with the sample 26 and collects the Raman scattered light from the sample. In another embodiment, more than one lens 28 or other optical element(s) may be located in the path of the incident beam 24 before the incident beam 24 contacts the sample 26.

In another embodiment, the means for directing the incident beam 24 toward the sample 26 comprises a dichroic beam-splitter mirror, such as shown in U.S. Pat. No. 7,403,281 to Carron et al. The incident beam 24 may be directed at the sample 26 without any intervening instrument components being located in the path of incident beam 24, or may be directed at a mirror, a holographic transmissive element, a mirror formed with a hole in the mirror or any other means for directing an incident beam known in the art. As described in U.S. Pat. No. 7,403,281, the spectrometer 20 may comprise a collimated beam tube, fiber optic waveguide or other optical elements to direct the incident beam 24 towards the sample 26.

The incident beam 24 induces or generates on contact with the sample 26 scattered radiation having an energy differential different from, and one or more wavelengths different than, the incident radiation 24, or the Raman shift that, for convenience, is described in this document as a Raman beam or signal 30 (or more generically a spectroscopy beam or signal for spectroscopic systems not limited to Raman spectroscopy systems). The Raman beam 30 is directed back into the spectrometer through an optical system of the spectrometer, such as at least a portion of the one used to direct the incident beam 24 to the sample 26. In the embodiment shown in FIG. 1, for example, the collection lens 28 receives the Raman beam 30 and directs the Raman beam through a long pass filter 32. The filtered Raman beam 30 is directed by a lens 34 through an aperture 36 and then collected by a lens 38 the Raman beam is then directed via a dispersing element 40 to another lens 42. The dispersing element 40 (e.g., a grating) is used to pass Raman regions through an aperture as the element 40 is rotated (or otherwise altered) to a position corresponding to a pertinent anticipated Raman region. The lens 42 focuses the beam on an aperture 44 and to one or more detectors 46. In one embodiment, for example, the aperture 44 comprises a two-dimensional aperture that passes "monochromatic" light that passes a small band of wavelengths to the detector 46.

Although FIG. 1 shows a single block corresponding to the detector 46, the spectrometer 20 may comprise a plurality of individual single channel detectors that together comprise the detector 46. Multiple pixels of a single multi-channel detector, for example, may each be treated as a single channel detector. In one embodiment, for example, each of the plurality of detectors 46 may be arranged (e.g., side by side) to receive one or more different frequencies from the dispersing element 40. The individual single channel detectors of the detector 46 may measure different spectral features (e.g., frequencies) of a spectroscopy signal in a single reading step, or a dispersing element may be adjusted (e.g., a grating rotated) to target different spectral features on the different single channel detectors of the detector 46.

FIG. 1 further shows a source synchronization component 48 (e.g., a lock-in amplifier system) that synchronizes the excitation source with the detector. In one embodiment, for example, the detector 46 comprises a synchronous detector in which a reference signal is used to drive (e.g., modulate) a light source at a particular frequency and the same frequency can be used to demodulate the detector signal. For example, a laser light source (e.g., a laser) can be modulated at a particular frequency (e.g., 100 KHz) and the detector may detect and demodulate the spectroscopy signal at the same frequency. In another embodiment, the detector may detect a signal over a narrow band of frequencies corresponding to the frequency used to modulate the light source. The synchronous detection may reduce or even eliminate a wide variety of spurious noise signals that are not within the narrow range of frequencies being sampled at the detector. Where a portable spectrometer is operated in day light, for example, the use of a source synchronization component, such as a lock-in amplifier, in the spectrometer can remove noise caused by taking a sample in daylight. Similarly, other noise signals may also be reduced or even eliminated to greatly increase the signal to noise ratio of the spectrometer.

FIG. 2 shows another example embodiment of a Raman spectrometer 50 that includes a calibration detector 52 for use in synchronizing the position of the grating to accurately target a desired spectral feature of a spectroscopic signal on the detector 46. The remaining elements of the Raman spectrometer 50 are the same as in the Raman spectrometer 20 shown in FIG. 1 and described above. In one embodiment, for example, a photodiode or other calibration detector 52 is used to determine (e.g., read) a position of the dispersing element 40 (e.g., a grating) before or as the anticipated Raman or other spectroscopic features are examined. In one particular embodiment, for example, a dispersing element (e.g., a grating) is used to pass Raman regions through an aperture as the element is rotated (or otherwise moved or altered) to a position corresponding to a pertinent anticipated Raman region.

One method of synchronizing the position of the grating to a targeted frequency of the spectroscopy signal comprises first mechanically locating a set point in the element's rotation (or other path). In one embodiment, for example, when a spectrometer is started up, prior to illuminating a sample or during a sample, a calibration signal is directed to a calibration detector 52 (e.g., a calibration photodiode) by the dispersing element 40. The calibration signal, for example, may comprise at least a spectral feature of an excitation signal (e.g., a laser signal) of the spectrometer, a spectroscopy signal received by the spectrometer, an internal reference frequency signal, or the like. An internal reference frequency, for example, may be provided using a diamond as an internal standard.

When the calibration detector detects the excitation signal (e.g., a peak signal corresponding to the excitation signal), the position of the dispersing element 40 can be identified as a set point. Thus, whether the dispersing element 40 has moved or the excitation signal has varied in frequency (e.g., drift), a set point for the dispersing element is identified. This set point can be used as a home position for the dispersing element before or during a spectroscopic measurement is taken.

From the set point, a position of the dispersing element 40 can be adjusted (e.g., by rotating a grating) to target a desired spectral feature of the spectroscopy signal onto one or more single channel detectors of the detector 46. A predetermined offset from the set point or home position of the dispersing element 40 can be used to adjust the dispersing element to a desired position. A grating dispersing element, for example, may be rotated, such as by a certain number of steps or degrees (the offset) from the set point or home position that was determined. The offset(s) (e.g., number of steps or degrees of rotation) are used to calibrate the position of the dispersing element to target one or more desired spectral features of the spectroscopic signal on one or more single channel detectors of the detector 46.

This method can be used, for example, to correct for changes in the mechanical stability of the spectrometer or for changes in the excitation frequency. In one example embodiment, for example, multimode or unlocked single mode diode lasers, which have been known to drift, can be used accurately by compensating for the laser frequency drift.

Figure 3:
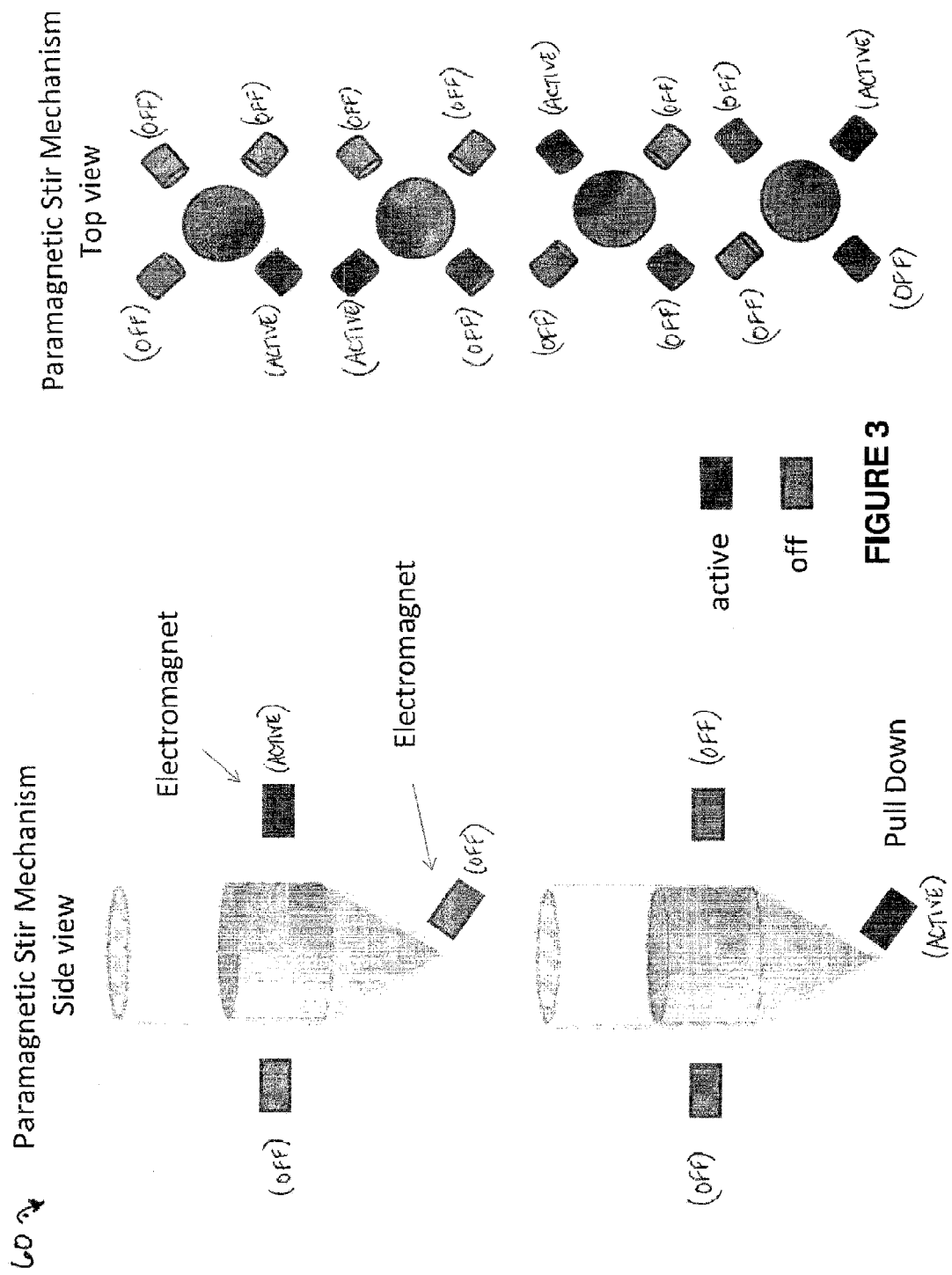
FIG. 3 shows views of an example embodiment of a paramagnetic stir system that can be used to stir tags with a sample and magnetically displace tagged analyte within the sample.

FIG. 3 shows views of an example embodiment of a paramagnetic stir system 60 that can be used to stir tags with a sample and magnetically displace tagged analyte within the sample. In this embodiment, for example, the system 60 is comparable to a DC motor that rotates an electromagnetic field and causes paramagnetic particles to move and create convection in a sample. The convection will also stir nonmagnetic Raman nanoparticles reporters/tags. After an appropriate stir phase, the particles can be displaced within the sample (e.g., pulled down as shown in FIG. 3) to a Raman assay region with an electromagnet, such as the pull-down electromagnet shown in FIG. 3. In other embodiments, magnets (e.g., permanent magnets or electromagnets) may be moved around a vial or other receptacle holding a sample to assist in stirring the sample. Similarly, the vial or other receptacle may be rotated within one or more magnets (e.g., permanent magnets or electromagnets) to assist in stirring a sample.

Figure 4:
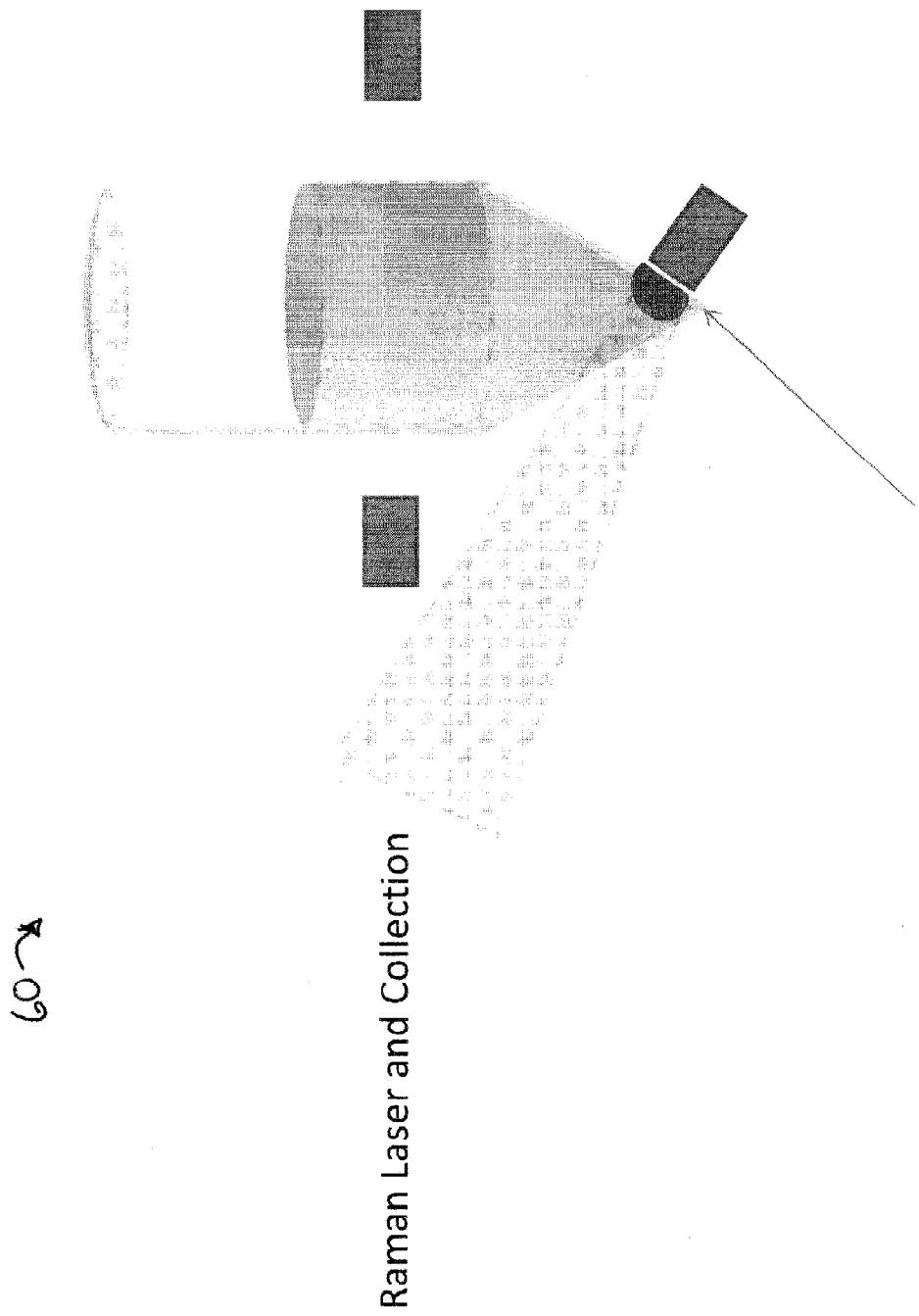
FIG. 4 shows another view of the paramagnetic stir system shown in FIG. 3 in which a plurality of paramagnetic particles and Raman tags/reporters have been displaced to the bottom of sample vial by activating an electromagnet near the bottom of the vial.

FIG. 4 shows another view of the paramagnetic stir system 60 shown in FIG. 3 in which a plurality of paramagnetic particles and Raman tags/reporters have been displaced to the bottom of sample vial by activating an electromagnet near the bottom of the vial. The Raman tags/reporters can be detected or "read" using a Raman reader in the vicinity of the vial bottom. In this embodiment, a "plug" of paramagnetic particles and any Raman reporters that have coupled to the paramagnetic particles may be formed at the bottom (or at another location) of the vial. The Raman reader transmits a laser beam to the region of the plug and will collect a Raman beam returned from the assay plug. It is also possible, with electromagnetic control, to oscillate the plug by turning the fields on and off. This could include, for example, turning the stirring magnets on and off in conjunction with the pull-down magnet. This would create a plug of material that is rotating in the vial. A Raman reading may be averaged over the plug as it rotates to search for one or more types of tags/reporters that have been captured in the plug.

In one embodiment, for example, a Raman reader may be positioned so that a laser excitation beam can be focused on the sample from the opposite side of the vial from the electromagnet, adjacent the electromagnet, through an aperture in the electromagnet, or from some other position where the laser beam of the Raman reader is able to be directed onto the sample in the bottom of the vial. In one particular embodiment, the paramagnetic system may provide for a no-wash assay even where the sample (e.g., whole blood) may be opaque.

Figure 5:
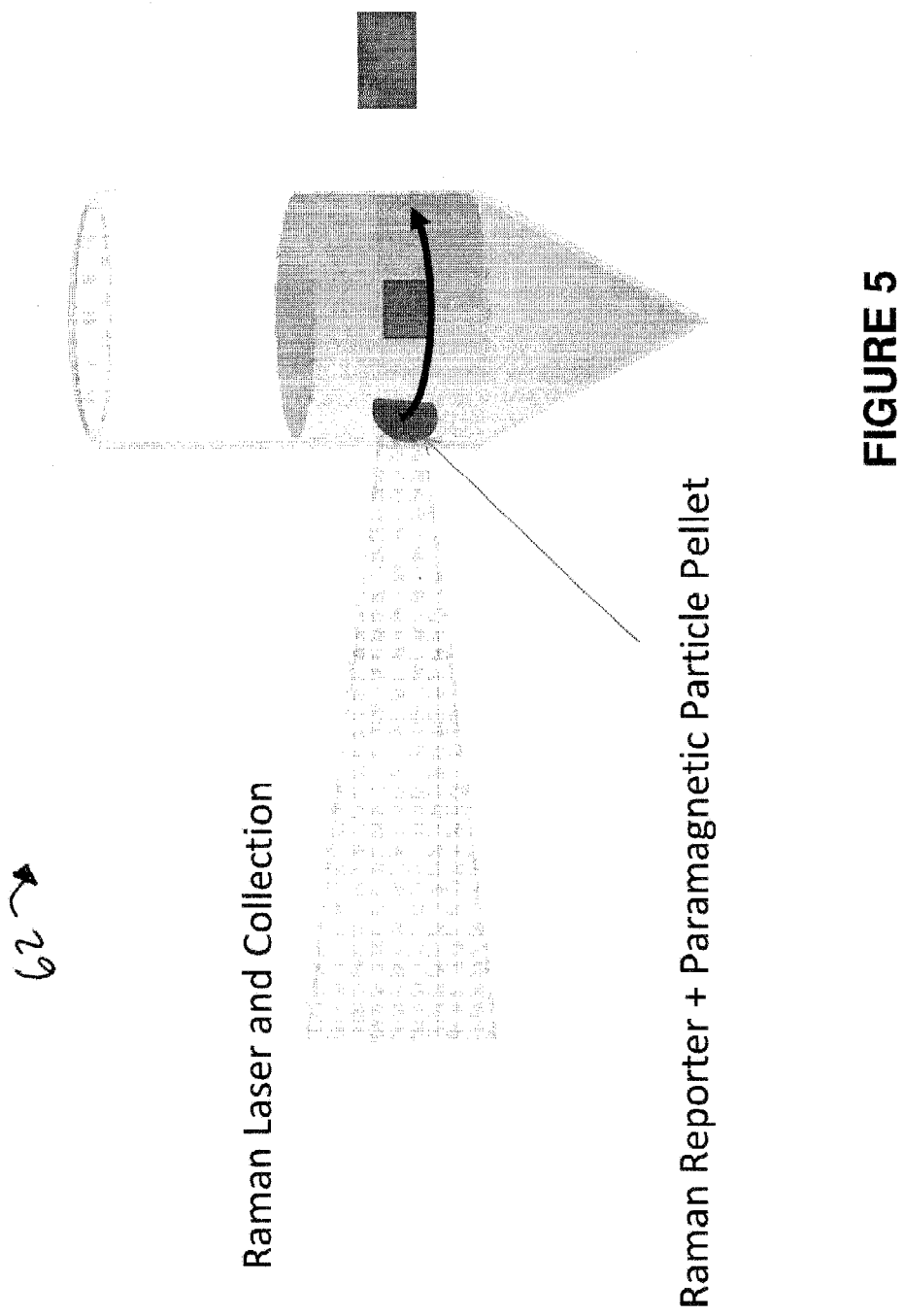
FIG. 5 shows another embodiment for analyzing magnetically captured tags/reporters.

FIG. 5 shows another embodiment of a system 62 for analyzing magnetically captured tags/reporters. In this embodiment, the magnetic fields are controlled to produce a rotating plug of material. The plug is analyzed by a Raman reader by directing a laser beam to the plug as the beam moves past the analysis point. This embodiment provides optical on-axis coupling of the laser and the spectrometer and may also provide good averaging over the magnetic material as it moves across the analysis point. At a low concentration, or in a multiplexed assay there may be a large number of magnetic particles that do not have tags/reporters bound to them.

FIG. 6 shows an example method 64 of performing an assay. In this example, three target pathogens (e.g., malaria, dengue fever, and typhoid) are being analyzed although any number of pathogens or other analytes may be analyzed. Each pathogen being tested has its own relevant Raman spectrum. A spectrum of the sample at a first time will show a weak signal for all of the pathogens. After stirring and localizing only those Raman tag/reporter particles that have bound to a paramagnetic particle will interact with a laser beam of a Raman reader and will be observed. In this particular example, a reader will check three regions of a Raman spectra and will observe a signal in a region for the Malaria active Raman tag/reporter. The Raman reader will translate the frequency calibrated signal versus the grating steps and report the correspondence between the strong signal at the steps that correspond to the Malaria active Raman tag/reporter.

Figure 8:
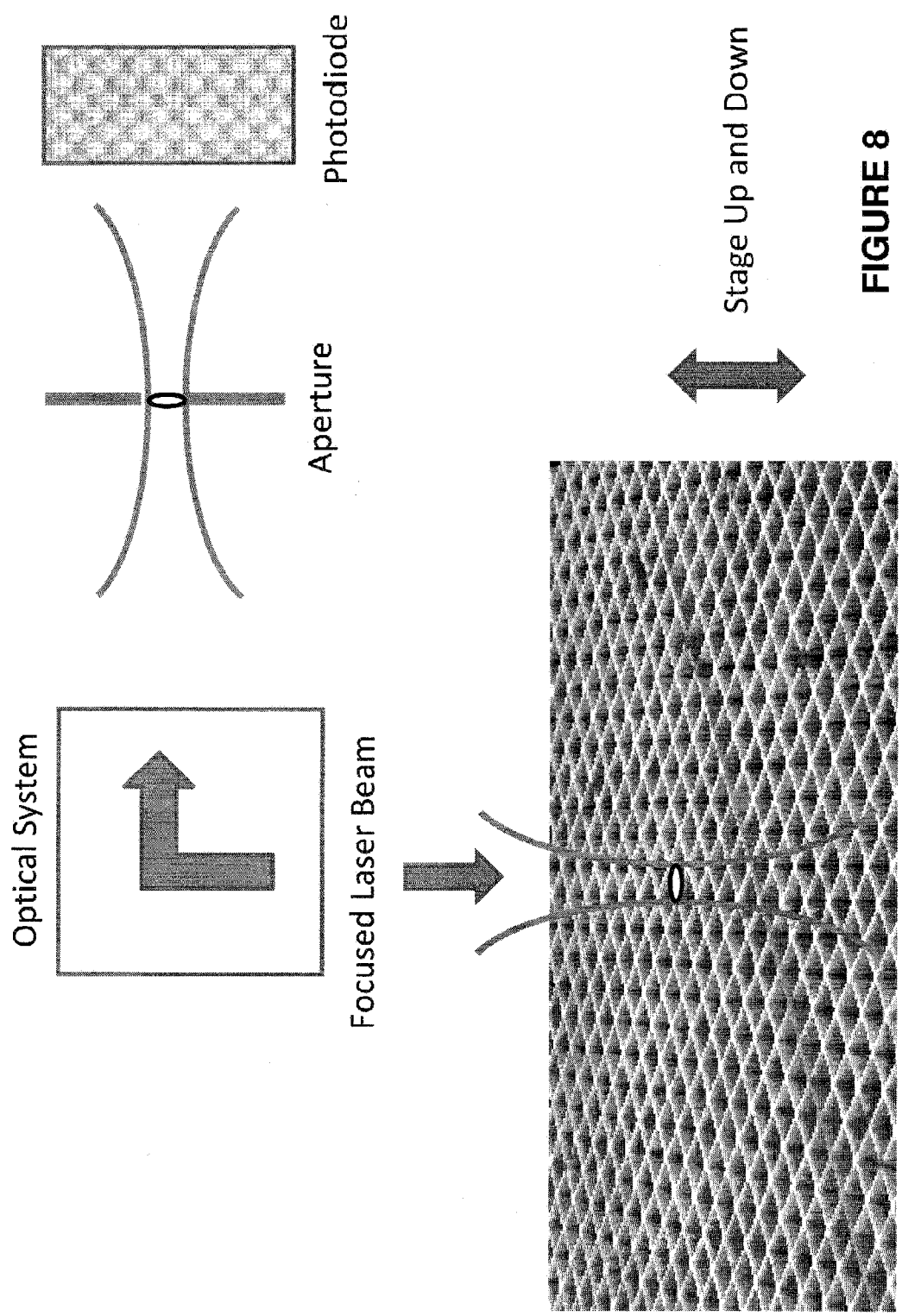

FIGS. 7 and 8 show an example method 66 and system 68 for three-dimensional imaging of Raman features of a sample. In this example, an optical system is used to focus a Raman beam on an aperture placed in front of a detector, such as a photodiode. If the aperture is placed so that it matches a waist of the Raman beam, an intensity of the beam returned to the detector will be maximum when that point is imaged directly through the aperture. By moving the aperture back and forth and/or moving a sample up and down (e.g., on a stage of a microscope), the spectrometer can be used to correlate the position to a map of the sample height and create a three-dimensional map of the sample. The optical system may comprise, for example, a confocal microscope or a Raman microscope. Although Raman microscopes exist, the time required to read a multichannel detector to map a surface in three dimensions is very long—on the scale of hours to a day. However, as described above, a single channel detector, such as a photodiode with phase sensitive detection can be used to achieve sampling times that are over a thousand times faster and would enable mapping a surface in minutes. For time sensitive samples or light sensitive samples, this may enable a three dimensional map that could not otherwise be performed with a standard Raman confocal system.

Figure 9:
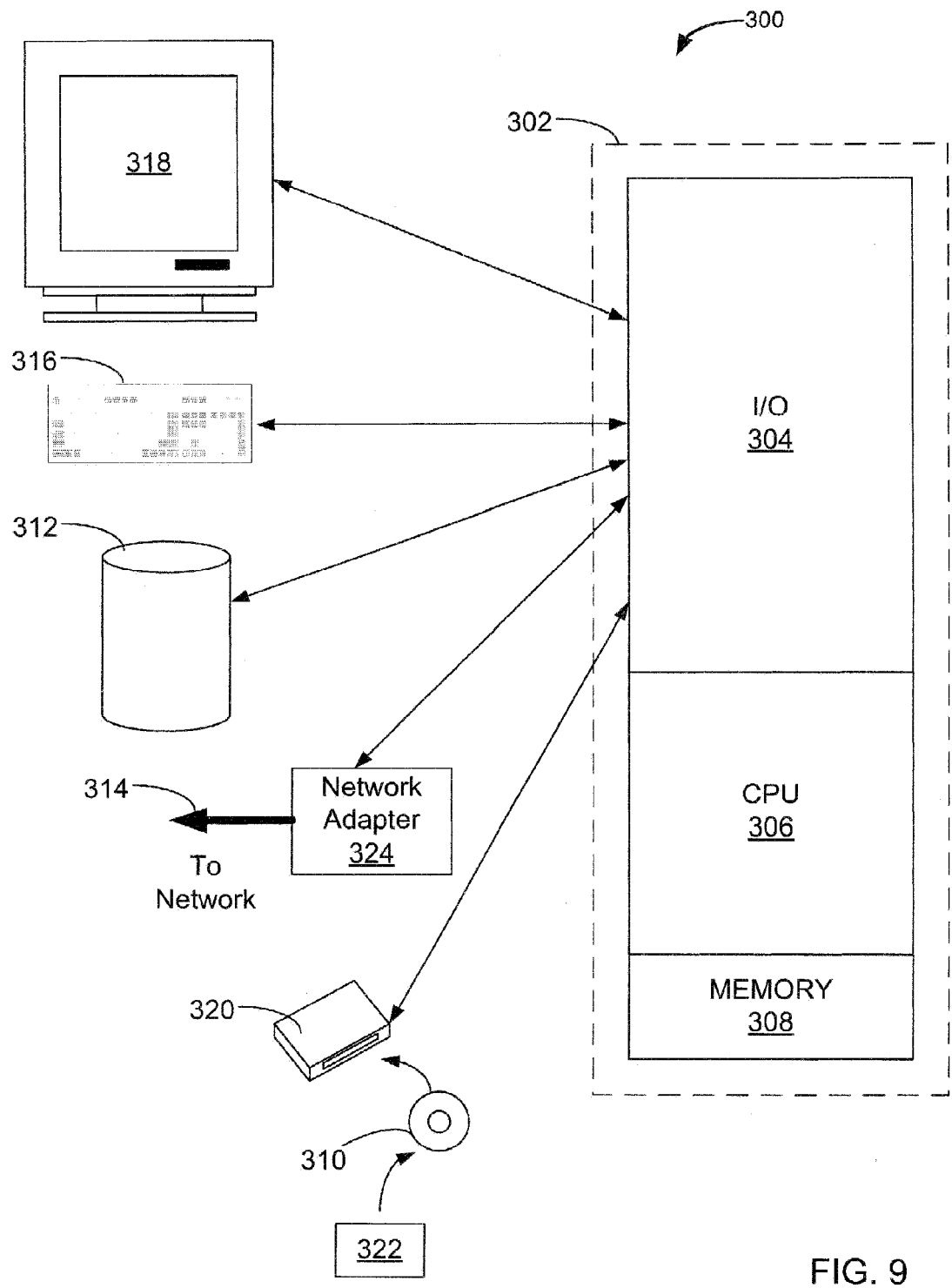
FIG. 9 illustrates an exemplary system useful in implementations of the described technology.

FIG. 9 illustrates an exemplary system useful in implementations of the described technology. A general purpose computer system 300 is capable of executing a computer program product to execute a computer process. Data and program files may be input to the computer system 300, which reads the files and executes the programs therein. Some of the elements of a general purpose computer system 300 are shown in FIG. 9 wherein a processor 302 is shown having an input/output (I/O) section 304, a Central Processing Unit (CPU) 306, and a memory section 308. There may be one or more processors 302, such that the processor 302 of the computer system 300 comprises a single central-processing unit 306, or a plurality of processing units, commonly referred to as a parallel processing environment. The computer system 300 may be a conventional computer, a distributed computer, or any other type of computer. The described technology is optionally implemented in software devices loaded in memory 308, stored on a data storage device (e.g., configured DVD/CD-ROM 310 or other storage unit 312), and/or communicated via a wired or wireless network link 314 on a carrier signal, thereby transforming the computer system 300 in FIG. 9 to a special purpose machine for implementing the described operations.

The I/O section 304 is connected to one or more user-interface devices (e.g., a keyboard 316 and a display unit 318), a disk storage unit 312, and a disk drive unit 320. Generally, in contemporary systems, the disk drive unit 320 is a DVD/CD-ROM drive unit capable of reading the DVD/CD-ROM medium 310, which typically contains programs and data 322. Computer program products containing mechanisms to effectuate the systems and methods in accordance with the described technology may reside in the memory section 304, on a disk storage unit 312, or on the DVD/CD-ROM medium 310 of such a system 300. Alternatively, a disk drive unit 320 may be replaced or supplemented by a floppy drive unit, a tape drive unit, or other storage medium drive unit. The network adapter 324 is capable of connecting the computer system to a network via the network link 314, through which the computer system can receive instructions and data embodied in a carrier wave. Examples of such systems include SPARC systems offered by Sun Microsystems, Inc., personal computers offered by Dell Corporation and by other manufacturers of Intel-compatible personal computers, PowerPC-based computing systems, ARM-based computing systems and other systems running a UNIX-based or other operating system. It should be understood that computing systems may also embody devices such as Personal Digital Assistants (PDAs), mobile phones, gaming consoles, set top boxes, Internet enabled televisions, etc.

When used in a LAN-networking environment, the computer system 300 is connected (by wired connection or wirelessly) to a local network through the network interface or adapter 324, which is one type of communications device. When used in a WAN-networking environment, the computer system 300 typically includes a modem, a network adapter, or any other type of communications device for establishing communications over the wide area network. In a networked environment, program modules depicted relative to the computer system 300 or portions thereof, may be stored in a remote memory storage device. It is appreciated that the network connections shown are exemplary and other devices or means of communications for establishing a communications link between the computers may be used.

In accordance with an implementation, software instructions and data directed toward providing synchronous detection and/or dispersing element calibration for a spectrometer, such as a Raman spectrometer, may reside on disk storage unit, disk drive unit or other storage medium units coupled to the system. The software instructions may also be executed by CPU 306.

The embodiments of the invention described herein are implemented as logical steps in one or more computer systems. The logical operations of the present invention are implemented (1) as a sequence of processor-implemented steps executing in one or more computer systems and (2) as interconnected machine or circuit modules within one or more computer systems. The implementation is a matter of choice, dependent on the performance requirements of the computer system implementing the invention. Accordingly, the logical operations making up the embodiments of the invention described herein are referred to variously as operations, steps, objects, or modules. Furthermore, it should be understood that logical operations may be performed in any order, unless explicitly claimed otherwise or a specific order is inherently necessitated by the claim language.

Although embodiments of this invention have been described above with a certain degree of particularity, those skilled in the art could make numerous alterations to the disclosed embodiments without departing from the spirit or scope of this invention. All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A spectroscopic system comprising:
   a light source adapted to provide a beam of illumination;
   an optical system adapted to provide the beam of illumination to a sample and receive a spectroscopy signal from the sample and direct the spectroscopy signal to at least one single channel detector, wherein the optical system comprises an adjustable dispersing element adapted to separate one or more spectral features from the spectroscopy signal and direct the one or more spectral features to the at least one single channel detector; and
   a source synchronization component adapted to synchronize an operation of the light source and the at least one single channel detector.

2. The spectroscopic system according to claim 1 wherein the optical system comprises a lens adapted to focus the beam of illumination on the sample.

3. The spectroscopic system according to claim 1 wherein the source synchronization component is adapted to modulate the beam of illumination at a modulation frequency and detect the spectroscopy signal over a band pass region corresponding to the modulation frequency.

4. The spectroscopic system according to claim 3 wherein the source synchronization component comprises a lock-in amplifier.

5. The spectroscopic system according to claim 1 wherein the at least one single channel detector comprises a plurality of single channel detectors that collectively provide a multichannel spectroscopic system.

6. The spectroscopic system according to claim 1 wherein light source of the spectroscopic system comprises an eye-safe laser at long wavelengths and the single channel detector comprises an extended InGaAs detector.

7. The spectroscopic system according to claim 1 wherein light source of the spectroscopic system comprises a laser at long wavelengths and the single channel detector comprises an InGaAs detector.

8. The spectroscopic system according to claim 1 wherein the spectroscopic system comprises a magnetic stir system.

9. The spectroscopic system according to claim 1 wherein the magnetic stir system comprises a system of electromagnets adapted to stir paramagnetic particles to increase a rate of a chemical reaction.

10. The spectroscopic system according to claim 9 wherein the chemical reaction comprises a biochemical reaction.

11. The spectroscopic system according to claim 1 wherein the spectroscopic system is configured to focus the beam of illumination on the sample displaced within an analyte by a magnetic displacement of paramagnetic particle components within the analyte.

12. The spectroscopic system according to claim 1 wherein the at least one single channel detector comprises a synchronous detector.

13. A spectroscopic system comprising:
    a light source adapted to provide a beam of illumination;
    an optical system adapted to provide the beam of illumination to a sample and receive a spectroscopy signal from the sample and direct the spectroscopy signal to at least one single channel detector, wherein the optical system comprises an adjustable dispersing element adapted to separate one or more spectral features from the spectroscopy signal and direct the one or more spectral features to the at least one single channel detector; and
    a calibration detector adapted to determine a set point of the adjustable dispersing element.

14. The spectroscopic system according to claim 13 wherein the calibration detector is adapted to determine the set point of the adjustable dispersing element corresponding to a detection of the beam of illumination at the calibration detector.

15. The spectroscopic system according to claim 13 wherein the calibration detector comprises a photodiode.

16. The spectroscopic system of claim 13 wherein a sample stage is configured to move the sample with correlation to the spectroscopy signal to produce a 3-dimensional map.

17. The spectroscopy system of claim 13 wherein the adjustable dispersing element is adapted to be controlled by using the set point as a home position for the adjustable dispersing element.

18. The spectroscopy system of claim 17 wherein the adjustable dispersing element is adapted to be adjusted from the set point to target the one or more spectral features of the spectroscopy signal onto the single channel detector.

* * * * *